US00PP23777P3

(12) United States Plant Patent
Nystrom

(10) Patent No.: US PP23,777 P3
(45) Date of Patent: Jul. 30, 2013

(54) APPLE TREE 'CN 121'

(50) Latin Name: *Malus domestica*
Varietal Denomination: CN 121

(76) Inventor: Charles Nystrom, Worthington, MN (US)

( * ) Notice: Subject to any disclaimer, the term of this patent is extended or adjusted under 35 U.S.C. 154(b) by 360 days.

(21) Appl. No.: 13/065,160

(22) Filed: Mar. 15, 2011

(65) Prior Publication Data

US 2012/0240294 P1 Sep. 20, 2012

(51) Int. Cl.
*A01H 5/00* (2006.01)

(52) U.S. Cl.
USPC ..... Plt./161

(58) Field of Classification Search
USPC ..... Plt./161
See application file for complete search history.

*Primary Examiner* — Wendy C Haas
(74) *Attorney, Agent, or Firm* — Paine Hamblen, LLP

(57) ABSTRACT

A new and distinct variety of apple tree '*Malus domestica*' which is denominated varietally as 'CN 121' and which produces an attractively colored apple which his mature for harvesting and shipment approximately September 19 under the ecological conditions prevailing near Ephrata, Wash., in the central portion of Washington State.

4 Drawing Sheets

Latin name: *Malus domestica.*
Varietal denomination: 'CN 121'.

BACKGROUND OF THE NEW VARIETY

The present invention relates to a new, novel, and distinct variety of apple tree, '*Malus domestica*,' and which has been denominated varietally as 'CN 121'.

ORIGIN

The present variety of apple tree resulted from an ongoing program of fruit breeding which was implemented by the inventor and a licensee. In this regard, seed from an open pollinated 'Honeycrisp' apple tree (U.S. Plant Pat. No. 7,197) were collected during the 1994 growing season. These seeds were germinated and the seedlings produced were subsequently grown to a stage of development where they were planted at an orchard which is located at Worthington, Minn. One seedling designated 'CN 121' was selected, in 2004, as having desirable characteristics. Subsequently, budwood was removed from this promising seedling and were then budded onto M26 rootstock (unpatented) in 2007. This M26 rootstock was then growing in the orchard of a licensee which is located near Ephrata, Wash. Subsequently, periodic evaluations of the trees and the fruit produced from this first asexually reproduced seedlings were compared to the fruit and other tree characteristics of the chance seedling 'CN 121' in 2009 and 2010, respectively. The subsequent evaluations of these first asexually produced trees have demonstrated that those asexually reproduced trees run true to the original chance seedling. All characteristics of the original tree, and its fruit, were established, and appear to be transmitted through the succeeding asexual propagations.

SUMMARY OF THE VARIETY

'CN 121' is a new and distinct variety of apple tree which is quite distinguishable from the closest known variety, that being, the 'Honeycrisp' apple tree (U.S. Plant Pat. No. 7,197)

from which it was derived as a chance seedling. In this regard, the fruit produced by the 'CN 121' apple tree develops an intense fruit skin color and pattern, whereas the fruit produced by the 'Honeycrisp' apple tree exhibits a striped pattern. In addition to the foregoing, the fruit produced by the new variety of apple tree ripens ten days later than the 'Honeycrisp' apple trees when grown at the same geographical location, and under the same cultural conditions. Moreover, internal indices of the new variety show that the fruit produced by this new apple tree has a greater fruit pressure; higher sugar content; higher pH; and lower titratable acid content as compared to the fruit produced by the 'Honeycrisp' apple tree (U.S. Plant Pat. No. 7,197).

BRIEF DESCRIPTION OF THE DRAWINGS

This new variety of apple tree is illustrated by the accompanying photographic drawings.

Figure 1:
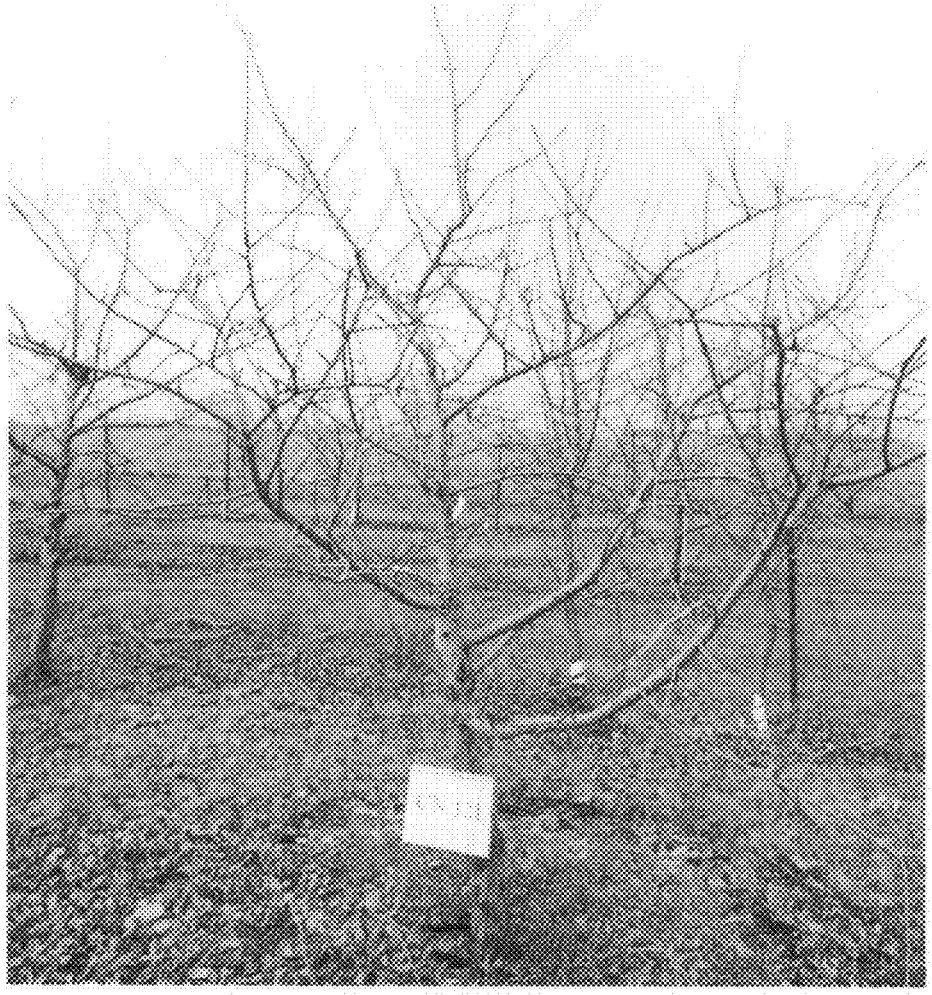
FIG. 1 is a picture of the original dormant 'CN 121' mother tree as currently seen in the orchard where it is growing.
Figure 2:
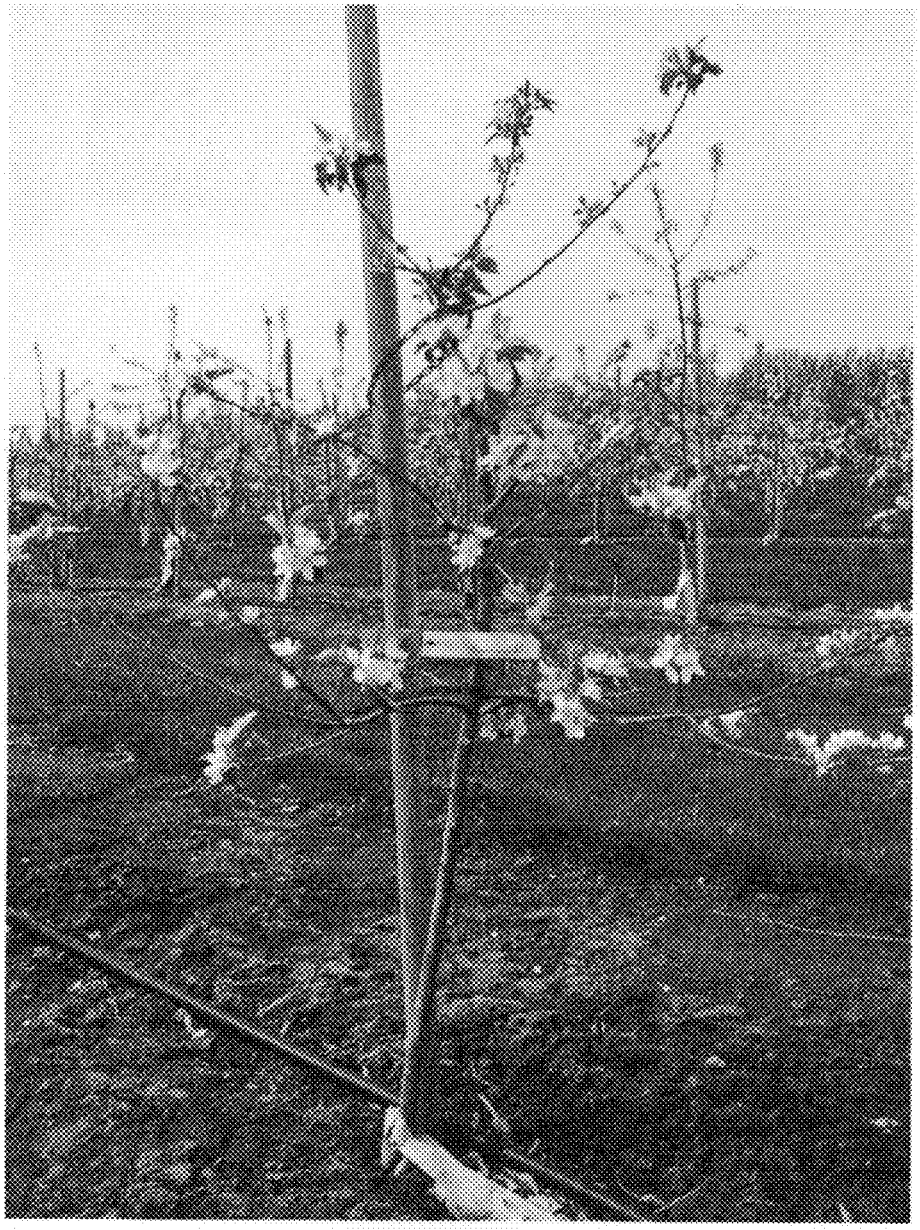
FIG. 2 is a picture of a second generation 'CN 121' apple tree shown at full bloom.
Figure 3:
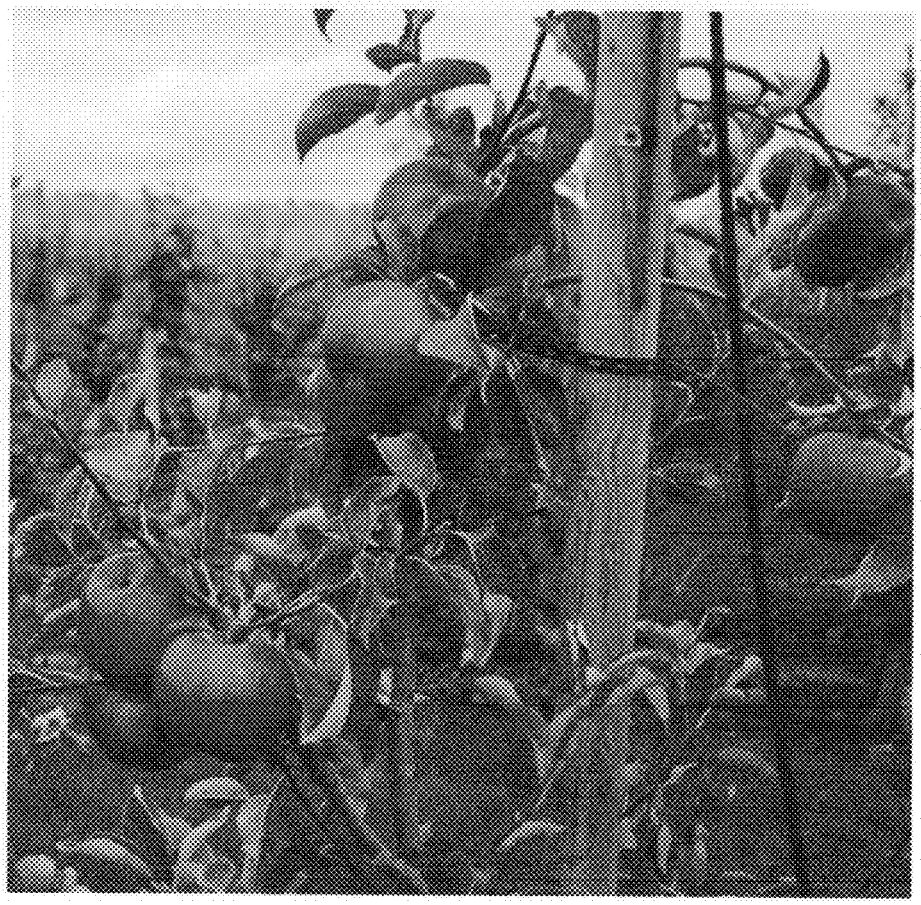
FIG. 3 shows the fruit produced by a mature, second generation, 'CN 121' apple tree.
Figure 4:
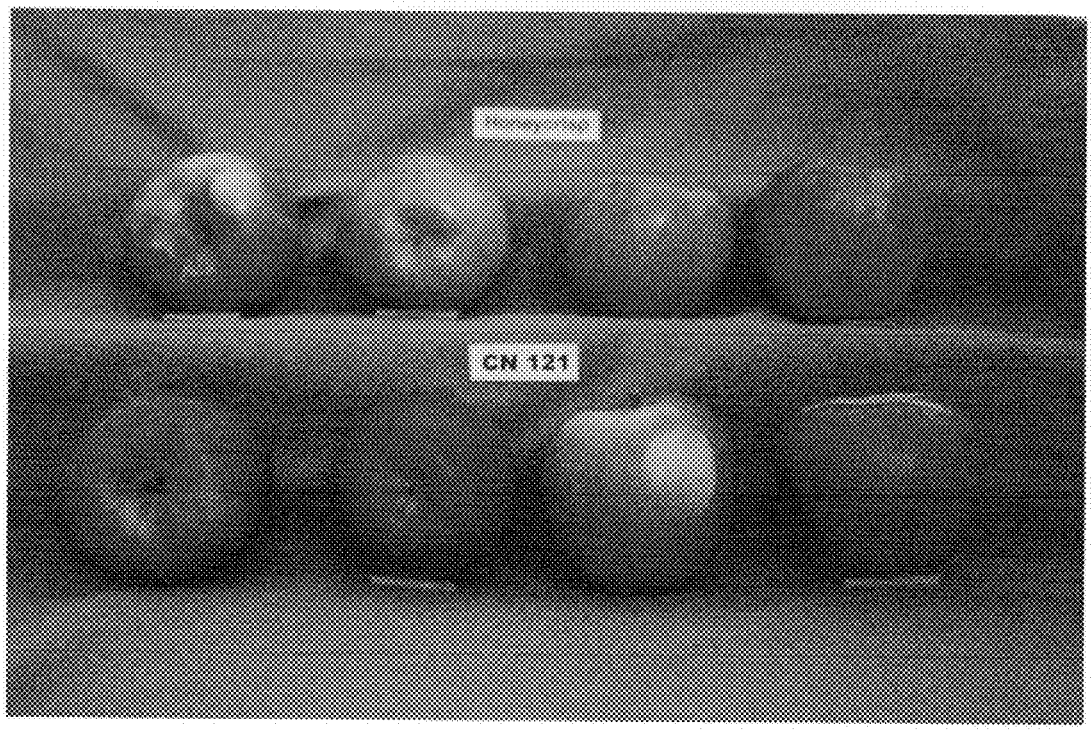
FIG. 4 depicts the fruit produced by a second generation 'CN 121' apple tree as compared to the fruit produced by a 'Honeycrisp' apple tree (U.S. Plant Pat. No. 7,197).

The colors in these photographs are as nearly true as is reasonably possible in a color representation of this type. Due to chemical development, processing, and printing, the leaves and fruit depicted in these photographs may, or may not, be accurate when compared to the actual specimen. For this reason, future color references should be made to the color plates (Royal Horticultural Society) and descriptions provided, hereinafter.

NOT A COMMERCIAL WARRANTY

The following detailed description has been prepared to solely comply with the provisions of 35 U.S.C. §112, and does not constitute a commercial warranty (either expressed or implied), that the present variety will, in the future, display the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole or in part to the present variety.

DETAILED DESCRIPTION

Referring more specifically to the pomological details of this new and distinct variety of apple tree, the following has been observed during the sixth fruiting season under the ecological conditions prevailing at the orchards of a licensee which are located near Ephrata, Wash. All major color code designations are by reference to The R.H.S. Colour Chart (Fourth Edition) provided by The Royal Horticultural Society of Great Britain. Common color names are also occasionally used.

TREE

*Size*.—Generally considered average as compared to other common apple cultivars. The current trees were pruned to a height of about 7.5 feet, and had a crown diameter of about 4.5 feet.

*Vigor*.—Considered moderate for the species.

*Tree form*.—Considered upright to upright spreading.

*Hardiness*.—Considered hardy with respect to U.S.D.A. Zone 6[a].

*Productivity*.—Considered average for the species.

*Trunk*.—Size — About 2.6 cm in diameter when measured at a height of about 20 cm above the graft union.

*Bark texture*.—Rough.

*Bark color*.—Gray/orange (RHS gray/orange group 165B).

*Lenticels*.—Generally — Present, and in moderate number. About 18 lenticels will be found in a four square centimeter area.

*Lenticels*.—Shape — Elongated.

*Lenticels*.—Width — About 0.3 mm to about 0.5 mm.

*Lenticels*.—Length — about 1.5 to 2.7 mm.

*Lenticels*.—Color — Orange/white (RHS 159B).

*First year branches*.—Diameter — When measured at the mid-point of growth the diameter is about 3.4 mm to about 4.4 mm.

*Color*.—Gray/orange (RHS Group N199C).

*Lenticels*.—Numbers — Considered numerous.

*Lenticels*.—Shape — Round, and about 0.2 mm in diameter.

*Lenticels*.—Color — White (RHS 155D).

*Branch pubescence*.—Generally — Considered present, and light in abundance.

*Branch pubescence*.—Color — Gray/orange (RHS Group 166A).

*Internodes*.—Size — About 3.1 cm to about 4.1 cm in width.

*Dormant fruiting buds*.—Shape — Considered conical.

*Dormant fruiting buds*.—Length — About 7.4 mm.

*Dormant fruiting buds*.—Basal Diameter — About 3.5 mm.

*Dormant fruiting buds*.—Color — Gray/orange (RHS 199C).

*Two year old fruiting branches*.—Size — Generally — About 5.8 mm to about 9.0 mm in diameter when measured at approximately the mid-point of the growth. Branch Color — Gray/brown (RHS Group 199A). Spur Development — Generally — Considered light. Spur Length — About 1 cm to about 2.9 cm in length. Spur Shape — Considered moderately acute.

*Lenticels*.—Numbers — Numerous, and averaging about 15 lenticels per square centimeter of surface area.

*Lenticels*.—Shape — Considered generally oval.

*Lenticels*.—Length — About 0.9 mm.

*Lenticels*.—Width — About 0.4 mm.

*Lenticels*.—Color — White (RHS Group 155D).

*Scaffold branches*.—Size — About 1 cm to about 1.3 cm in diameter when measured at a distance of about 10 cm from the trunk.

*Scaffold branches*.—Crotch Angle — As currently trained in the orchard, the crotch angle is about 45 degrees from the vertical. However, this characteristic should not be considered distinctive of the present variety.

*Scaffold branches*.—Color — Gray/brown (RHS N199C).

*Scaffold branches*.—Lenticels — Numerous lenticels are present. On average, about 8 lenticels appear per square centimeter of surface area.

*Scaffold branch lenticels*.—Shape — Elongated and small.

*Scaffold branch lenticels*.—Size — About 0.7 mm in width and in length.

*Scaffold branch lenticels*.—Color — Orange/white (RHS Group 159C).

LEAVES

*Leaf shape*.—Generally — Considered broadly acute and generally upwardly folded.

*Leaf texture*.—Dorsal Surface — Considered leathery and slightly undulating.

*Leaf texture*.—Lower Surface — Considered glabrous.

*Surface sheen*.—The dorsal surface has a high sheen. The ventral surface has a somewhat dull appearance.

*Pubescence*.—Generally — The pubescence appears on the ventral surface only, and covers substantially the entire surface.

*Pubescence*.—Texture — Considered fine.

*Pubescence*.—Color — White (RHS 155C).

*Leaves*.—Length — Variable from about 77 mm to about 100 mm.

*Leaves*.—Width — About 48 mm to about 62.8 mm.

*Leaves*.—Marginal Form — Considered mostly serrate, although occasionally bi-serrate portions will be seen.

*Leaf tip shape*.—Generally — Considered acuminate.

*Leaves*.—Base Shape — Considered rounded.

*Leaves*.—Stipules — Generally absent. On occasion one will be found on a petiole. Stipules — Length — About 7.1 mm. Stipules — Width — About 1.1 mm. Stipules — Color — The dorsal and ventral surfaces both have a yellow-green color (RHS 147B).

*Leaf pubescence*.—Generally — The Pubescence is generally present on the ventral surfaces, but it is considered fine in texture. The leaf pubescence only covers about 50% of the ventral leaf surface.

*Leaf pubescence*.—Color — White (RHS 155C).

*Leaf blade color.*—Dorsal Surface — Yellow/green (RHS 147A).
*Leaf blade color.*—Ventral Surface — Yellow/green (RHS 147C).
*Leaf midvein.*—Shape — Considered prominent, and having a fine pubescence on its ventral surface.
*Leaf mid-vein.*—Width — When measured at midblade it is about 1.1 mm in width.
*Mid-vein color.*—Dorsal Surface — Gray/yellow (RHS 160C).
*Mid-vein pubescence.*—Color — White (RHS 155C).
*Petiole.*—Length — About 20.2 to 35.4 mm.
*Petiole.*—Diameter. When measured at the mid-point, it is about 1.3 to 1.7 mm.
*Petiole.*—Color — Yellow/Green (RHS 147D). Further highlights of gray/red (RHS 181A) are seen at the basal end thereof.
*Petiole.*—Pubescence — Generally it is considered abundant, and having a fine texture over the entire length and circumference of the petiole.
*Pubescence color.*—White (RHS 155C).

FLOWERS

*Date of full bloom.*—In 2010, the date of full bloom was April 27.
*Number of blossoms per bud.*—Generally 5 to 6 blossoms will be found per bud.
*Flower size.*—Generally — Considered medium to medium large.
*Flower diameter.*—At full expansion it is about 43 to about 51 mm.
*Flower petals.*—Width — About 20 to about 23 mm.
*Flower petals.*—Length — About 14 to about 19 mm.
*Flower petals.*—Color — White (RHS 155B). Further, the flower petals may have highlights of gray/purple (RHS 186D).
*Petal vein color.*—Gray/purple (RHS 186B).
*Flower stamen.*—Numbers — About 18 to 20 stamens will be found.
*Filament.*—Length — About 5.2 to 11.8 mm.
*Filament color.*—Yellow (RHS Group 2D).
*Anthers.*—Shape — Kidney shaped.
*Anthers.*—Width — About 1.6 mm.
*Anthers.*—Length — About 1.7 mm.
*Anthers.*—Color — At full maturity the anthers gray/yellow (RHS 160C).
*Pistil.*—Length — About 14.3 to about 16.1 mm.
*Styles.*—Numbers — Typically 5, and they are usually fused at the middle.
*Styles.*—Color — They are usually white, and pubescent below the union.
*Styles.*—Length — About 6.9 to about 8.7 mm.
*Styles.*—Color — Yellow/green (RHS 144C).
*Stigma.*—Shape — Club-like.
*Stigma.*—Color — Gray/yellow (RHS 162A).
*Sepals.*—Numbers — Typically 5 per blossom are found.
*Sepals.*—Form — Usually the sepals are curled back towards the peduncle.
*Sepals.*—Shape — Considered deltoid.
*Sepal tip.*—Shape — Acuminate.
*Sepal base.*—Shape — Truncate.
*Sepals.*—Length — About 8.4 mm.
*Sepals.*—Width — About 3.8 mm.
*Sepal pubescence.*—Generally speaking this is present on both the dorsal and ventral surfaces.
*Sepal color.*—Green (RHS 146C). Further the tips of the sepals are typically highlighted with a gray/orange color (RHS 165A).
*Peduncle.*—Length — About 16 to about 20 mm.
*Peduncle.*—Color — Yellow/green (RHS 144A). Occasionally a yellow/green color (RHS 152A) appears along the mid-ribs of the peduncle.

FRUIT

*Maturity when described.*—Ripe for harvesting and shipment about Sep. 19, 2010. This harvesting date was 10 days later than the apple tree 'Honeycrisp' which was growing at the same geographical location and under similar cultural conditions.
*Fruit form.*—Considered mostly conical, and occasionally round, with about 50% of the fruit appearing lopsided. The equatorial cross-sectional shape is irregular.
*Fruit size.*—Considered medium to medium large under normal crop loads.
*Equatorial fruit diameter.*—About 83.6 mm.
*Axial diameter.*—About 74.5 mm.
*Fruit stem.*—Length — Considered medium, about 22.1 mm.
*Fruit stem.*—Diameter — About 2.4 mm.
*Stem cavity.*—Average Width — About 34.3 mm.
*Stem cavity.*—Average Depth — About 19.3 mm.
*Stem cavity.*—Shape — Acute.
*Stem cavity.*—Form — No lipping is apparent.
*Basin cavity.*—Average width — About 28.7 mm.
*Basin cavity.*—Average depth — About 10.3 mm.
*Basin cavity sides.*—Shape — Rounded.
*Eye.*—Generally considered erect.
*Sepal.*—Color — White (RHS 155C) and appearing downy in appearance.
*Fruit skin.*—Surface — Considered glabrous and a light bloom is present.
*Fruit skin.*—Appearance — Considered washed out, especially on the side of the fruit which is not directly exposed to sunlight.
*Fruit color.*—Generally — The overall color is more intense on exposed sides.
*Skin color.*—Overcolor — Red (RHS 46A).
*Skin color.*—Undercolor — Yellow/green (RHS 150C).
*Fruit skin thickness.*—Generally — Medium.
*Fruit skin texture.*—Considered tough.
*Fruit skin lenticels.*—Generally — Scattered, small, and considered indistinct and more numerous towards the Calyx end of the fruit.
*Lenticels.*—Numbers — About 3 per cm square are found when measured at the stem end, and 10 per cm square when this is measured at the Calyx end.
*Lenticels.*—Surface Texture — Smooth. The skin appears areolar in appearance.
*Lenticels.*—Surface Color — White (RHS N155D).
*Lenticels.*—Size — About 0.2 to about 0.4 mm in diameter but otherwise considered round.
*Fruit core.*—Position — Considered distant.
*Fruit core.*—Line position — Basal clasping.
*Fruit core.*—Diameter — About 32.7 mm.
*Fruit core.*—Length — About 26.9 mm.
*Fruit core.*—Shape — Considered flat and conical.

*Fruit cell.*—Numbers — 5.

*Fruit cell.*—Form — Considered tufted, and narrow lines circumvent the cell walls.

*Tuft.*—Color — The tufting is white (RHS 155C).

*Fruit cell.*—Shape — Considered elliptical.

*Fruit cell.*—Length — About 17.1 mm.; Fruit Cell — Width — about 9.3 mm.

*Fruit cell.*—Depth — About 7 mm.

*Tube.*—Shape — Cone-like.

*Stamen position.*—Generally considered medium.

*Axis.*—The cells are axially disposed and considered open.

*Seeds.*—Numbers — 1-2 seeds are found, mostly 2.

*Seed shape.*—Generally — Considered mostly acute, and some approaching acuminate in shape.

*Seed length.*—About 8.3 to 8.9 mm.

*Seed width.*—About 4 mm to about 5.3 mm.

*Seed color.*—Brown (RHS Group 200B).

*Fruit flesh.*—Generally — Considered firm, crisp, melting, sweet, sub-acid and juicy.

*Flesh texture.*—Considered medium coarse grained.

*Flesh color.*—White (RHS 155A).

*Flesh aroma.*—Apple-like, and mild in intensity.

*Fruit pressure.*—The new variety of apple tree produces fruit having a fruit pressure of about 17.5 pounds. This is higher than the fruit pressure produced by the fruit of the 'Honeycrisp' apple tree. When that tree is grown under the same ecological conditions its fruit has a pressure of about 13.76 pounds.

*Brix.*—The new variety of apple tree, at commercial maturity, produces fruit having a brix of about 14.6. This brix is higher than that produced by the fruit of the 'Honeycrisp' apple tree (U.S. Plant Pat. No. 7,197) which, when grown under the same ecological conditions, has a brix of about 13.8.

*pH.*—At commercial maturity, the fruit of the present variety of apple tree has a pH of about 3.43. This pH is lower than that produced by the fruit of the 'Honeycrisp' apple tree (U.S. Plant Pat. No. 7,197) which, at full commercial maturity, and grown under the same ecological conditions, has a pH of about 3.35.

*Fruit keeping quality.*—Considered excellent. The fruit of the present variety has been kept up to five months in cold storage with no deleterious effects noted.

*Pollination.*—The present variety may be pollinated by any diploid apple tree that blooms at approximately the same season.

*Fruit use.*—Considered a fresh desert apple.

*Disease and insects resistance.*—The present variety is considered to be susceptible to all insects and diseases found in the region of central Washington.

Although the new variety of apple tree which is described herein possesses the aforementioned characteristics when grown under the ecological conditions prevailing near Ephrata, Wash., in the central part of Washington State, it should be understood that variations of the usual magnitude and characteristics incident to changes in growing conditions, fertilization, pruning, pest control, frost and climatic variables and other horticultural management practices are to be expected.

Having thus described and illustrated my new variety of apple tree, what I claim is new, and desire to secure by Plant Letters Patent is:

1. A new and distinct variety of apple tree, substantially as illustrated and described and which is characterized principally as to novelty by producing an attractively colored apple which is ripe for harvesting and shipment on or before September $19^{th}$ under the ecological conditions prevailing near Ephrata, Wash. in the central part of Washington State.

* * * * *